US005750125A

United States Patent [19]

Lahanas et al.

[11] Patent Number: 5,750,125
[45] Date of Patent: May 12, 1998

[54] CLEAR COSMETIC STICKS AND PROCESS FOR ITS PREPARATION

[75] Inventors: Konstantinos M. Lahanas, Paramus, N.J.; Daniela Toma, Floral Park, N.Y.; Andrew J. Bevacqua, East Setauket, N.Y.; Gheorghe Cioca, Lake Grove, N.Y.

[73] Assignee: Estee Lauder, Inc., New York, N.Y.

[21] Appl. No.: 666,750

[22] Filed: Jun. 19, 1996

[51] Int. Cl.$^6$ .............................. A61K 7/00; A61K 7/32; A61K 7/42
[52] U.S. Cl. .................. 424/401; 424/59; 424/65; 424/405; 424/407; 424/409; 424/DIG. 5
[58] Field of Search .................... 424/59, 65, 405, 424/407, 409, DIG. 5

[56] References Cited

U.S. PATENT DOCUMENTS

| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |
| 4,822,602 | 4/1989 | Sabatelle | 424/65 |

*Primary Examiner*—Shelley A. Dodson
*Attorney, Agent, or Firm*—Fish & Neave; Richard M. Barnes; Brett G. Alten

[57] ABSTRACT

The present invention relates to compositions that are stable, solid, and clear and suitable for topical application to human skin and to methods for preparing and using such compositions. The compositions of the invention comprise dibenzyl monosorbitol acetal (DBMSA) and a refractory material having a refractive index of between about 1.50 and about 1.65.

40 Claims, No Drawings

CLEAR COSMETIC STICKS AND PROCESS FOR ITS PREPARATION

TECHNICAL FIELD OF THE INVENTION

The present invention relates to clear, solid compositions suitable for topical application to human skin and to methods for making and using such compositions. The compositions of the invention comprise dibenzyl monosorbitol acetal (DBMSA), and a refractory material containing a carrier fluid and preferably one or more cosmetic materials, the refractory material having an index of refraction between about 1.50 and about 1.65.

BACKGROUND OF THE INVENTION

Dibenzyl monosorbitol acetal, herein referred to as DBMSA, is a known gelling agent. For example, DBMSA has been used as a gelling agent in transparent or translucent deodorant and antiperspirant sticks. See, for example, U.S. Pat. Nos. 4,154,816, 4,346,079, 4,518,582, 4,725,430, 4,743,444, 4,816,261, and 4,781,917 and European patent applications 260,030 and 451,002. One difficulty with achieving commercially useful DBMSA-based cosmetic compositions arises from the fact that the concentration of DBMSA in a particular composition influences the hardness and clarity of the composition, as well as the level of product transfer to the skin upon application. In general, an increase in the concentration of DBMSA will provide a harder, less transparent composition, and a lower level of product transfer to the skin upon application. Conversely, a decrease in the concentration of DBMSA will provide a softer, more transparent composition, and a higher level of product transfer to the skin upon application.

Other difficulties arise with the methods for making and using compositions suitable for topical application to human skin. For example, solvents are typically used in deodorant and antiperspirant sticks to solubilize DBMSA at elevated temperatures. One class of solvents are hydrophilic solvents (e.g., solvents which are capable of uniting with or absorbing water), such as lower monohydric alcohols. However, the use of hydrophilic solvents to solubilize DBMSA in many compositions containing cosmetic colorants, fragrances, sunscreens or dermatologic agents poses a number of problems. First, hydrophilic solvents are generally irritating and are undesirable in compositions for use on areas having mucus membranes (e.g., the areas around the lips or eyes). Second, hydrophilic solvents are generally incompatible with lipophilic colorants that are frequently used in cosmetic preparations. Third, lower monohydric alcohols, such as ethanol, are incompatible with certain sun care and antiinflammatory agents because they adversely effect the skin protective qualities of these agents. And finally, the flammable nature of alcohols at high concentrations makes the use of such monohydric alcohols for topical application to human skin particularly undesirable.

Lipophilic solvents are also used in certain deodorant and antiperspirant sticks to solubilize the DBMSA at elevated temperatures. These compositions are often prepared by adding together one or more lipophilic waxes to a mixture of a DBMSA and one or more lipophilic solvents. The lipophilic wax-containing compositions are then transferred to suitable containers for cooling and solidification. Frequently, however, compositions containing high levels of lipophilic waxes are not clear and have a hazy or darkened appearance which blocks the true color of the cosmetic or dermatologic agents in the composition. Furthermore, high levels of lipophilic waxes are perceived to be excessively sticky or greasy upon application.

It is therefore an object of the present invention to provide substantially transparent, non-irritating, DBMSA-based solid cosmetic compositions. It is a further object of the present invention to provide such compositions that can transfer a high level of product to the skin upon application. It is another object of the present invention to provide such compositions that contain, in addition to DBMSA, a refractory material comprising a carrier fluid and preferably one or more cosmetic materials, the refractory material having an index of refraction of between about 1.50 and about 1.65. It is yet a further object of this invention to provide substantially transparent, non-irritating, DBMSA-based solid cosmetic compositions that are not perceived as being sticky or greasy. An additional object of this invention is to provide methods for preparing such compositions.

SUMMARY OF THE INVENTION

The compositions of the present invention consists of:
(1) DBMSA in an amount from about 0.5% by weight to about 30% by weight of the composition; and
(2) a refractory material in an amount from about 70% by weight to about 99.5% by weight of the composition, the refractory material having a refractive index between about 1.50 and about 1.65 and comprising a carrier fluid in an amount from about 50.0% by weight to about 99.0% by weight of the composition.

Preferably, the refractory material also comprises a cosmetic material in an amount from about 0.5% by weight to about 20.0% by weight of the composition, the cosmetic material being selected from the group consisting of colorants, fragrances, sunscreens, dermatologic agents, and mixtures thereof.

As used herein, a carrier fluid includes materials (including mixtures of materials) that are fluids at elevated temperatures (i.e., flowable materials) and that are capable of dissolving DBMSA. Preferred materials for use in the carrier fluid are materials that exhibit an index of refraction from about 1.50 to about 1.65. Examples of such materials are octyl methoxycinnamate, phenoxy ethanol, benzyl alcohol, phenyl trimethicone, and methyl benzoate, with octyl methoxycinnamate being particularly preferred for use as a carrier fluid.

The compositions of the invention may be made by a method which comprises the steps of:
(a) mixing DBMSA with the carrier fluid at a temperature and for a period of time sufficient (e.g., at a temperature of between about 75° C. and about 200° C. for about 15 min to about 45 min) to dissolve the DBMSA in the carrier fluid to form a solution; and
(b) cooling said composition to ambient temperature.

Preferably, the method further includes a step of mixing a cosmetic material selected from the group consisting of colorants, fragrances, sunscreens, dermatologic agents and mixtures thereof with the solution to form the composition, the amounts of DBMSA, carrier fluid, and cosmetic material being adjusted such that the resulting mixture contains:
(i) DBMSA in an amount from about 0.5% by weight to about 30% by weight of the composition,
(ii) the refractory material in an amount from about 70% by weight to about 99.5% by weight of the composition,
(iii) the carrier fluid in an amount from about 50.0% by weight to about 99.0% by weight of the composition, and (iv) the cosmetic material in an amount from about 0.5% by weight to about 20.0% by weight of the composition.

It is to be understood that the step of mixing a cosmetic material, set forth above, may be conducted prior to the DBMSA being dissolved in the carrier fluid, or during or after the dissolution step. It is also to be understood that step (a) may be conducted in steps. For example, the DBMSA may be first mixed with a first component of the carrier fluid at a temperature and for a period of time sufficient to dissolve the DBMSA in the first component to form a first solution. Then, the first solution may be combined with a second component of the carrier fluid at a temperature and for a period of time sufficient to form a second solution. It should be understood that because the carrier fluid may have more than two components, yet additional carrier fluid components may be added to this second solution.

It will also be understood that the cosmetic material may be mixed with the other ingredients of the invention (e.g., DBMSA or one or more components of the carrier fluid) before or after the DBMSA is dissolved in the carrier fluid or while the dissolution step is being conducted.

The compositions of the invention preferably use a lipophilic oil as the only or primary carrier fluid in the composition. Such compositions are substantially non-greasy and non-sticky. Most preferably, at least 80% by weight of the refractory material is a lipophilic oil (as opposed to a lipophilic wax) to achieve a composition that is substantially non-greasy and non-sticky.

DETAILED DESCRIPTION OF THE INVENTION

While not wishing to be bound by any theory, we believe that at room temperature the DBMSA-based compositions of the invention contain a solid phase and a fluid phase. The solid phase comprises a three-dimensional network of crystallized DBMSA fibers. The refractory material is in the fluid phase, which we believe coexists between the DBMSA fibers. We further believe that the clarity of our DBMSA-based compositions is attributable to a substantial extent on our using a refractory material that has an index of refraction close to the index of refraction of the DBMSA network.

Preferred compositions of the invention comprises DBMSA in an amount from about 2.0% by weight to about 5.0% by weight of the composition. DBMSA suitable for use in the invention may be obtained from a number of commercial sources. Among the commercially available sources of DBMSA are MILLITHIX™ 925 (obtained from Milliken Chemical, a division of Milliken & Company, Spartansburg, S.C.), GELL-All-D™ (obtained from New Japan Chemical Company, Ltd.), and DISORBENE™ (obtained from ROQUETTE Freres, France.)

Preferably, refractory material is present in the compositions of the invention in an amount from about 70% by weight to about 99.5% by weight of the composition. Most preferably, the index of refraction of the refractory material is between about 1.53 and about 1.57.

The indices of refraction of the materials used in this invention (e.g., DBMSA, refractory materials, carrier fluids, cosmetic materials, as well as the components and mixtures thereof) may be measured by using a refractometer, and by employing conventional refractometry techniques. A particularly preferred refractometer for the determination of the index of refraction of materials used in accordance with this invention is Fisher Scientific's Abbe Refractometer Model No. 6182 (This and other models of Abbe refractometers are commercially available from Fisher Scientific, of Springfield, N.J.). As used herein, any material, including any solid, liquid, or mixture thereof, is said to be "refractory" if the material has an index of refraction between about 1.50 and about 1.65, when measured at 25° C. and atmospheric pressure.

Refractory carrier fluids suitable for use in the invention may be prepared from one, two, or more components, with the individual components in the mixture possibly being either refractory or non-refractory and being in the form of a solid or liquid at room temperature. Some examples of solids at room temperature that may be components of the carrier fluid are truxillic acid, ferulic acid, and ethyl ferulate. Examples of liquids which may be used as components of the carrier fluid include the class of liquids miscible at elevated temperatures with DBMSA, such as octyl methoxycinnamate, phenyl trimethicone, phenoxy ethanol, benzyl alcohol, dibenzyl maleate, and methyl benzoate.

A wide range of non-refractory components, such as many lipophilic materials can be used as a component of the refractory carrier fluid for use in our invention. A lipophilic material, as used herein, refers to a non-polar material that is miscible in lipids. One class of lipophilic fluids that may be used in the present invention is the class known as cosmetically acceptable esters, e.g., mono-, di- and tri-esters having an alcohol chain length of 1 to 22 and an acid chain length of 1 to 22. Persons skilled in the art recognize that the group of cosmetically acceptable esters is very large, and can be further subdivided into, e.g., oils, waxes, glyceryl esters aliphatic esters and fats. See, e.g., *CFTA International Cosmetic Ingredient Dictionary*, 4th ed. (J. M. Nikitakis, et al. eds. Cosmetic, Toiletry and Fragrance Association, Inc. Washington, 1991). It is understood that although many of the cosmetically acceptable esters are non-refractory, some cosmetically acceptable esters are refractory by themselves.

Preferably at least about 80% by weight, most preferably at least about 95% by weight of the carrier fluid is one or more lipophilic oils. As used herein, the term lipophilic oils, refers to lipophilic materials that are liquid at room temperature to about 25° C. Preferred lipophilic oils for use in the invention are selected from the group consisting of castor oil, mineral oil, squalene, fatty acids (e.g., oleic acid), fatty alcohols (e.g., octyldodecanol), a $C_{12-15}$ alkyl benzoate, a propylene glycol dipelargonate, a glycerol trioctanoate and mixtures thereof.

The carrier fluid may also contain a lipophilic wax. Preferably, no more than about 20% by weight of the refractory material is one or more lipophilic waxes, particularly where non-greasy and non-sticky compositions are desired. As used herein, the term lipophilic waxes, refers to lipophilic materials that are solid at room temperature, but melt at elevated temperatures. Preferred lipophilic waxes are those selected from the group consisting of insect waxes, such as beeswax, animal waxes, such as lanolin, plant waxes, such as carnauba, mineral waxes, such as ozokerite, petroleum waxes, such as paraffin wax, synthetic waxes, such as polyethylene, and mixtures thereof.

Colorants useful in the composition of the invention include lipophilic dyes, lakes, pigments and mixtures thereof. Preferred fragrances are the essential oils. Dermatological agents that may be used in our compositions include vitamins, antiinflammatory agents, hydroxyacids, and the like, and mixtures thereof. Sunscreens that may be used include dioxybenzone, 2-ethylhexyl 2-cyano-3,3-diphenylacrylate, 2-ethylhexyl p-methoxycinnamate, 2-ethylhexyl salicylate, homosalate, menthyl anthranilate, oxybenzone, octyl dimethyl PABA, red petrolatum, titanium dioxide, ferulic acid esters, or mixtures thereof. Preferably the sunscreen is titanium dioxide, ferulic acid esters or mixtures thereof. Most preferably the sunscreen is titanium dioxide or ethyl ferulate or mixtures thereof.

The specific composition and amount of the refractory material that is used for the compositions of the invention is a function of the aesthetic and functional properties desired. The aesthetic and functional properties that may be controlled by a person skilled in the art by varying the composition and amount of refractory material include, for example, emolliency, skin feel, and rate of absorbance through the skin.

The carrier fluid used in compositions of this invention may also comprise other ingredients that are commonly employed by one of skill in the art in compositions for application to the skin (e.g., stabilizers, antimicrobial agents, antioxidants, and the like).

In a preferred embodiment of making the compositions of this invention, the DBMSA and the refractory material are combined and heated at a temperature sufficient to dissolve substantially all the DBMSA before one or more cosmetic materials are added to the mixture. Preferably, the temperature used is about 75° C. to about 200° C., most preferably about 150° C. to about 200° C. Once substantially all the DBMSA is in solution, the cosmetic material is combined with the solution and the resulting mixture is cooled to room temperature. Particularly when the cosmetic material is colored or particulate, proceeding in this manner facilitates the ability of the person(s) making the composition to determine that substantially all the DBMSA is dissolved in the solution.

Preferably, the cooling step is conducted after the composition is transferred while still above ambient temperature, to the container in which it will be stored. For example, heated, still liquid material may be transferred to a lipstick mold, a makeup pan, or a wide-mouthed jar and cooled to ambient temperature to solidify the mixture.

Another method for preparing compositions of the present invention includes the step of mixing DBMSA and a first component of a multi-component carrier fluid. The first component may be a solvent which, when combined with DBMSA at a temperature and for a period of time (e.g., about 15 min to about 45 min), is sufficient to dissolve the DBMSA in the solvent to form a first solution. Appropriate first components include the class of solvents known as hydrogen bond accepting solvents, i.e., solvents which are capable of accepting hydrogen bonds of other molecules and include, for example, 3-methyl-2-oxozolidone, N-methylpyrrolidone, N,N-diethyl-3-methylbenzamide, and phenoxy ethanol. Phenoxy ethanol is most preferred.

The first solution is mixed with a second component of the carrier fluid at a temperature and for a period of time (e.g., about 15 min to about 45 min) sufficient to dissolve the first solution in the second component of the carrier fluid to form a second solution. Then, preferably, a cosmetic material selected from the group consisting of colorants, fragrances, sunscreens, dermatologic agents and mixtures thereof, in the desired amount, is mixed with the second solution to form the composition. Upon mixture of the cosmetic material to the second solution, additional heating may be required to ensure proper blending of the resulting composition. Thereafter, the resulting composition is cooled to ambient temperature.

The DBMSA and the refractory material may be combined and mixed together using any means familiar to those skilled in the art. For example, a LIGHTNIN™ Stirrer or a Silverson homogenizer may be used for this purpose. The mixing step is carefully monitored (e.g., by close visual inspection) to ensure that the solution is substantially free of undissolved DBMSA.

Preferably, the compositions of the present invention may be formulated for a wide range of cosmetic applications. For example, the compositions may be formulated as lip area treatment preparations, eye area treatment preparations, sunscreen preparations, antiinflammatory preparations, antiacne preparations, antibacterial preparations, color cosmetic preparations, fragrance preparations, moisturizing preparations, exfoliating preparations, and the like.

The following non-limiting examples illustrate various compositions of the present invention.

EXAMPLES

Example 1

| A Clear Lipstick with Color | | |
|---|---|---|
| | Component | Parts By Weight |
| Phase 1: | Phenoxy ethanol | 85.00 |
| | DBMSA | 14.50 |
| Phase 2: | D & C Red No. 21 6921/362[1] | 0.50 |

[1] A D & C Red No. 21-containing composition obtained from Sun Chemical Corp.

Procedure:

Phase 1 was blended at 175° C. using a LIGHTNIN™ Mixer until a clear solution was obtained. Phase 2 was then mixed into this solution. The resultant mixture was poured into a mold and cooled to room temperature.

The procedure of Example 1 was also used to prepare the compositions of Examples 3–5.

Example 2

| A Clear Lipstick | | |
|---|---|---|
| | Component | Parts By Weight |
| Phase 1: | Octyl methoxycinnamate | 95.00 |
| Phase 2: | DBMSA | 5.00 |

Phase 1 was heated to 175° C. and mixed with phase 2 using a LIGHTNIN™ Mixer. The resultant mixture was poured into a lipstick mold and cooled to room temperature.

The composition of Example 2 is useful for providing an aesthetically pleasing, non-sticky, non-greasy, clear composition to the lip area.

Example 3

| A Sunscreen Stick | | |
|---|---|---|
| | Component | Parts By Weight |
| Phase 1: | Phenyl trimethicone | 87.50 |
| | DBMSA | 5.00 |
| Phase 2: | Octyl methoxycinnamate | 7.50 |

Example 4

A Sunscreen Stick

| | Component | Parts By Weight |
|---|---|---|
| Phase 1: | Phenyl trimethicone | 85.50 |
| | DBMSA | 5.00 |
| Phase 2: | Salicylic acid USP (Powder)[2] | 2.00 |
| | Octyl methoxycinnamate | 7.50 |

[2] A salicylic acid-containing composition obtained from Rhone-Poulenc Inc.

Example 5

A Sunscreen Stick

| | Component | Parts By Weight |
|---|---|---|
| Phase 1: | Finsolve TN[3] | 75.00 |
| | DBMSA | 5.00 |
| Phase 2: | Ferulic acid | 20.00 |

[3] A $C_{12-15}$ alkyl benzoate-containing composition obtained from Finetex, Inc.

The Sun Protection Factors (SPF) of sunscreen stick Examples 3–5 can be measured using the in vivo method (See: "Sunscreen Products for Over-The-Counter Human Drugs, Proposed Safety, Effective and Labeling Conditions", Department of Health, Education, and Welfare, Food and Drug Admin., Federal Register 43(166), Part II, pp. 38206–38269 (1978)).

Example 6

A Solid Fragrance Stick

| | Component | Parts by Weight |
|---|---|---|
| Phase 1: | Emerest 2388[4] | 95.00 |
| | DBMSA | 4.50 |
| Phase 2: | Fragrance | 0.50 |

[4] A propylene glycol dipelargonate-containing composition obtained from Henkel Corp.

Phase 1 was blended at 175° C. using a LIGHTNIN™ Mixer until a clear solution was obtained. Phase 2 was then mixed into this solution. The resultant mixture was poured into a mold and cooled to room temperature.

While the present invention has been set forth in terms of specific embodiments thereof, it will be understood that the invention is the defined by the appended claims.

We claim:

1. A solid, substantially clear composition suitable for topical application to human skin, which consists of:
   (1) DBMSA in an amount from about 0.5% by weight to about 30% by weight of the composition; and
   (2) a refractory material in an amount from about 70% by weight to about 99.5% by weight of the composition, said refractory material having a refractive index between about 1.50 and about 1.65 and said refractory material comprising a carrier fluid in an amount from about 50.0% by weight to about 99.0% by weight of the composition.

2. The composition according to claim 1 wherein the refractory material further comprises a cosmetic material in an amount from about 0.5% by weight to about 20.0% by weight of the composition, said cosmetic material being selected from the group consisting of colorants, fragrances, sunscreens, dermatologic agents, and mixtures thereof.

3. The composition according to claim 1 wherein the carrier fluid comprises at least one refractory component.

4. The composition according to claim 3 wherein the at least one refractory component is selected from the group consisting of octyl methoxycinnamate, phenoxy ethanol, phenyl trimethicone, benzyl alcohol, dibenzyl maleate, methyl benzoate, and mixtures thereof.

5. The composition according to claim 4 wherein the at least one refractory component is phenoxy ethanol.

6. The composition according to claim 4 wherein the at least one refractory component is octyl methoxycinnamate.

7. The composition according to claim 3 wherein the at least one refractory component is selected from the group consisting of truxillic acid, ferulic acid, ethyl ferulate, and mixtures thereof.

8. The composition according to claim 1 wherein said carrier fluid comprises a lipophilic oil.

9. The composition according to claim 8 wherein the lipophilic oil is selected from the group consisting of castor oil, mineral oil, squalene, fatty acids, fatty alcohols, a $C_{12-15}$ alkyl benzoate, a propylene glycol dipelargonate, a glycerol trioctanoate and mixtures thereof.

10. The composition according to claim 9 wherein the lipophilic oil is a $C_{12-15}$ alkyl benzoate.

11. The composition according to claim 9 wherein the lipophilic oil is a propylene glycol dipelargonate.

12. The composition according to claim 9 wherein the lipophilic oil is a glycerol trioctanoate.

13. The composition according to claim 1 wherein the carrier fluid comprises a lipophilic wax selected from the group consisting of animal waxes, insect waxes, plant waxes, mineral waxes, petroleum waxes, synthetic waxes and mixtures thereof.

14. The composition according to claim 2 wherein the cosmetic material is a colorant selected from the group consisting of lipophilic dyes, lakes, pigments and mixtures thereof.

15. The composition according to claim 2 wherein the cosmetic material is a dermatologic agent selected from the group consisting of vitamins, antiinflammatory agents, hydroxyacids and mixtures thereof.

16. The composition according to claim 15 wherein the dermatologic agent is a hydroxyacid.

17. The composition according to claim 2 wherein the cosmetic material comprises a sunscreen selected from the group consisting of dioxybenzone, 2-ethylhexyl 2-cyano-3, 3-diphenylacrylate, 2-ethylhexyl p-methoxycinnamate, 2-ethylhexyl salicylate, homosalate, menthyl anthranilate, oxybenzone, octyl dimethyl PABA, red petrolatum, titanium dioxide, ferulic acid esters and mixtures thereof.

18. The composition according to claim 17 wherein the sunscreen comprises ethyl ferulate.

19. The composition according to claim 17 wherein the sunscreen is titanium dioxide.

20. A method for preparing a solid, substantially clear composition for topical application to the skin, the composition consisting of DBMSA and a refractory material, said refractory material comprising a carrier fluid and a cosmetic material, the method comprising the steps of:
   (a) mixing DBMSA with at least the carrier fluid at a temperature and for a period of time sufficient to dissolve the DBMSA in the carrier fluid to form a solution; and
   (b) cooling said composition to ambient temperature.

21. The method according to claim 20, further comprising the step of mixing a cosmetic material selected from the group consisting of colorants, fragrances, sunscreens, dermatologic agents and mixtures thereof with the solution to form the composition, the amounts of DBMSA, carrier fluid, and cosmetic material being adjusted such that the resulting mixture contains DBMSA in an amount from about 0.5% by weight to about 30% by weight of the composition, a refractory material in an amount from about 70% by weight to about 99.5% by weight of the composition, the refractory material comprising a carrier fluid in an amount from about 50.0% by weight to about 99.0% by weight of the composition, and a cosmetic material in an amount from about 0.5% by weight to about 20.0% by weight of the composition.

22. The method according to claim 20 wherein step (a) is conducted at a temperature between about 75° C. and about 200° C.

23. The method according to claim 21 wherein said step of mixing a cosmetic material is conducted prior to, during or after the DBMSA is dissolved in the carrier fluid.

24. The method according to claim 21 wherein the DBMSA is dissolved in the carrier fluid before said step of mixing a cosmetic component is conducted.

25. The method according to claim 20, wherein the carrier fluid comprises a first component and a second component wherein:

(a) DBMSA and the first component are mixed together at a temperature and for a period of time sufficient to dissolve the DBMSA in the first component to form a first solution; and (b) the first solution is mixed with the second component at a temperature and for a period of time sufficient to dissolve the first solution in the second component, to form a second solution.

26. The method of claim 25 wherein said method further comprises the step of mixing a cosmetic material with said second solution.

27. The method according to claim 25 wherein the first component is selected from the group consisting of 3-methyl-2-oxazolidone, n-methyl pyrrolidone, n,n-diethyl-3-methylbenzamide, phenoxy ethanol, and mixtures thereof.

28. The method according to claim 27 wherein the first component is phenoxy ethanol.

29. The method according to claim 27 wherein the component is 3-methyl-2-oxazolidone.

30. The method according to claim 25 wherein step (a) is conducted at a temperature between about 75° C. and about 200° C.

31. A composition prepared according to the method of claim 20.

32. A composition prepared according to the method of claim 21.

33. A composition prepared according to the method of claim 24.

34. A composition prepared according to the method of claim 25.

35. A method for applying a cosmetic composition to the skin comprising the step of applying to the skin the composition of claim 1.

36. A method for applying a cosmetic composition to the skin comprising the step of applying to the skin the composition of claim 2.

37. A method for applying a cosmetic composition to the skin comprising the step of applying to the skin the composition of claim 4.

38. A method for applying a cosmetic composition to the skin comprising the step of applying to the skin the composition of claim 6.

39. A method for applying a cosmetic composition to the skin comprising the step of applying to the skin the composition of claim 9.

40. A method for applying a cosmetic composition to the skin comprising the step of applying to the skin the composition of claim 17.

* * * * *

UNITED STATES PATENT AND TRADEMARK OFFICE
CERTIFICATE OF CORRECTION

PATENT NO. : 5,750,125
DATED : May 12, 1998
INVENTOR(S) : Konstantinos M. Lahanas et al It is certified that error appears in the above-identified patent and that said Letters Patent is hereby corrected as shown below:

On the title page, item [56] add the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 5 | 2 | 7 | 0 | 0 | 3 | 4 | 9/1995 | Cheng | | | |
| | | | | | | | | | | | | | |

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | W | O | 92/ | 1 | 9 | 22 | 1 | 11/1992 | PCT Int'l Appl. | | | | |
| | | 0 | 67 | 36 | 4 | 2 | A | 1 | 9/1995 | Europe | | | | |

Signed and Sealed this

Ninth Day of February, 1999

Attest:

Attesting Officer

*Acting Commissioner of Patents and Trademarks*